United States Patent
Koehler et al.

(10) Patent No.: US 10,379,085 B2
(45) Date of Patent: Aug. 13, 2019

(54) ASSEMBLY FOR NONDESTRUCTIVE MATERIAL TESTING

(71) Applicant: FRAUNHOFER-GESELLSCHAFT ZUR FOERDERUNG DER ANGEWANDTEN FORSCHUNG E.V., Munich (DE)

(72) Inventors: Bernd Koehler, Dresden (DE); Frank Schubert, Dresden (DE); Uwe Lieske, Dresden (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 134 days.

(21) Appl. No.: 15/313,717

(22) PCT Filed: May 26, 2015

(86) PCT No.: PCT/EP2015/061564
§ 371 (c)(1),
(2) Date: Mar. 30, 2017

(87) PCT Pub. No.: WO2015/181152
PCT Pub. Date: Dec. 3, 2015

(65) Prior Publication Data
US 2017/0205374 A1  Jul. 20, 2017

Related U.S. Application Data

(63) Continuation of application No. PCT/EP2015/061564, filed on May 26, 2015.

(30) Foreign Application Priority Data

May 26, 2014 (DE) .................. 10 2014 209 990

(51) Int. Cl.
B06B 1/06 (2006.01)
G01N 29/04 (2006.01)
(Continued)

(52) U.S. Cl.
CPC ............. G01N 29/041 (2013.01); B06B 1/06 (2013.01); G01N 29/2437 (2013.01);
(Continued)

(58) Field of Classification Search
CPC ............. G01N 29/041; G01N 29/2437; G01N 2291/0422; G01N 2291/105; G01N 2291/106; H01L 41/082; B06B 1/06
See application file for complete search history.

(56) References Cited

U.S. PATENT DOCUMENTS 5,625,149 A   4/1997   Gurururaja et al.
6,048,622 A   4/2000   Hagood, IV et al.
(Continued)

FOREIGN PATENT DOCUMENTS

DE   19861017   6/2000
DE   19937479   3/2001
(Continued)

OTHER PUBLICATIONS 1-3 Piezo Composites & Tranducers for Ultrasound Applications, Apr. 27, 2014, pp. 1-8, XP055206534, URL: http://www.smart-material.com/media/Datasheet/13K_V2.0-2014.pdf.

Primary Examiner — Justin Seo
Assistant Examiner — John M Royston
(74) Attorney, Agent, or Firm — Jacobson Holman, PLLC.

(57) ABSTRACT

The invention relates to an assembly for nondestructive material testing with which shear waves are emitted and detected in elastic surfaces of components or workpieces, in which piezoelectric transducer elements are arranged above
(Continued)

Figure 1:
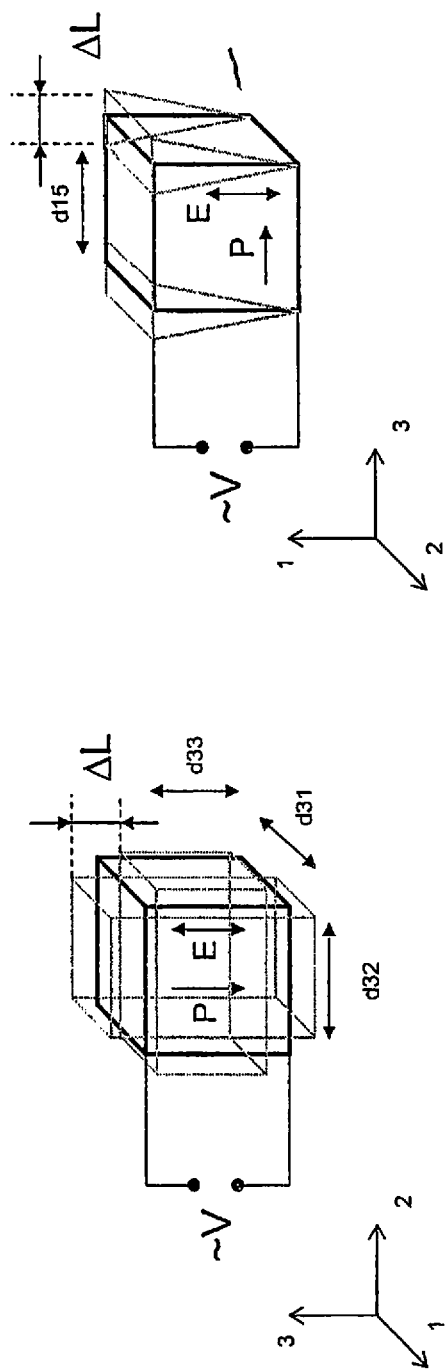

one another in multiple planes and the piezoelectric transducer elements arranged in adjacent planes can each be operated oppositely to one another. The piezoelectric transducer elements can be piezoelectric fibers and/or piezoelectric plate-like elements that are connected to or embedded in an elastically deformable material.

9 Claims, 4 Drawing Sheets

(51) Int. Cl.
    *G01N 29/24*     (2006.01)
    *H01L 41/08*     (2006.01)

(52) U.S. Cl.
    CPC .... *H01L 41/082* (2013.01); *G01N 2291/0422* (2013.01); *G01N 2291/105* (2013.01); *G01N 2291/106* (2013.01)

(56) References Cited

U.S. PATENT DOCUMENTS

| | | | |
|---|---|---|---|
| 6,629,341 B2 * | 10/2003 | Wilkie | H01L 41/082 |
| | | | 156/222 |
| 2008/0143216 A1 | 6/2008 | Berkcan et al. | |
| 2009/0236940 A1 * | 9/2009 | Nakayama | B06B 1/064 |
| | | | 310/336 |

FOREIGN PATENT DOCUMENTS

| | | |
|---|---|---|
| EP | 1983574 | 10/2008 |
| EP | 1983584 A2 | 10/2008 |

* cited by examiner ically ineffectively using the known
ASSEMBLY FOR NONDESTRUCTIVE MATERIAL TESTING The invention relates to an assembly for nondestructive material testing by which shear waves are emitted and detected in elastic surfaces of components or workpieces. Piezoelectric transducer elements are used in this process.

Piezoelectric transducers are used in nondestructive material testing for emitting and coupling elastomechanical waves into a workpiece to be tested. The formation of shear waves is required and advantageous for certain test work. These shear waves effect particle deflections perpendicular to their direction of propagation. Two polarizations are possible in this process, namely vertically polarized shear waves (SV) and horizontally polarized shear waves (SH). With horizontally polarized shear waves, the direction of vibration is in the entry plane. Such SH waves are in particular suitable for detecting cracks, as a form of defects, in pipe lines and weld seams. SH waves are free of dispersion and are therefore very far-reaching. In addition, they do not interact with fluid media that are outwardly or inwardly adjacent to the component.

SH shear waves can be formed by utilizing the shear effect in piezoelectric materials or by the use of electromagnetic ultrasound transducers. The invention is in this respect directed to improvements in the formation of shear waves using piezoelectric transducers.

The fact is disadvantageous with piezoelectric transducers in which the shear is triggered by the d15 effect that the upper transducer side has to be loaded by a relatively large seismic mass or that a fixing, by which shear is hindered, has to be carried out at the transducer so that the shear waves can be transmitted into the workpiece to be tested.

The piezoelectric effect links electrical and mechanical values to one another. A mechanical deformation is converted by the piezoceramic material into an electrical signal, and vice versa. The sensor and actuator behavior of these materials allows a plurality of applications in the field of electrical engineering acoustics, automation engineering, communications engineering, in automotive engineering and in further areas of use. Piezoceramic sensors and actuators as well as complex piezoceramic assemblies and systems are used in this respect.

The deformation caused by applying an electric voltage and forming an electrical field is typically characterized by indices in Vogt notation, with the first index indicating the cause, i.e. the direction of the electrical field, and the second index indicating the effect, i.e. the direction of the deformation of the piezoelectric material.

Applications are possible, in addition to the use of piezoelectric transducers as thickness vibrators (d33), i.e. applying an electrical field in the direction of the polarization of the transducer or the lateral length change caused by transverse contraction (d31, d32), in which a shear of the transducer is desired. The upper side and lower side of the transducer shear in opposite directions by forming an electrical field transversely to the polarization axis (d15). If one of these transducer surfaces is applied to the examination object by means of adhesive bonding or by means of highly viscous liquids and if the counter-side is held mechanically or via inertia, horizontal forces are introduced into the object that excite SH shear waves. The SH shear waves have previously been formed by means of the d15 effect in this process.

Options and corresponding deformations are shown in FIG. 1.

An alternative to piezoelectric transducers is represented by electromagnetic ultrasound transducers that can likewise be used to introduce surface-parallel forces into metallic surfaces. This is inter alia based on the Lorenz effect and on magnetorestriction, but requires an electrical conductivity of the examination object/workpiece.

Piezoelectric fibers are used to provide thin, flexible and light sensors. In addition, the transverse contraction of a transducer can be kept low by them and a deformation mainly in the longitudinal fiber direction can be achieved. A length change of the piezoelectric fiber can take place by two options in this process. On the one hand, an electrical field directed in parallel with the polarization in each case can be generated by an alternating polarization in the longitudinal fiber direction and using electrode fingers at each of which an alternating, changing electric voltage is applied, whereby a length change of the piezoelectric fiber can be achieved (d33, FIG. 2, left). On the other hand, a length change can be achieved by a piezoelectric fiber polarized in the thickness direction and by forming an electrical field across the fiber thickness (d31, FIG. 2, right).

Figure 3:
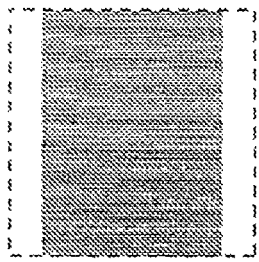
Figure 3:
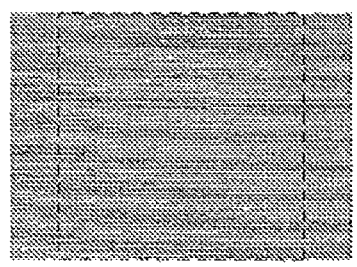
Figure 3:
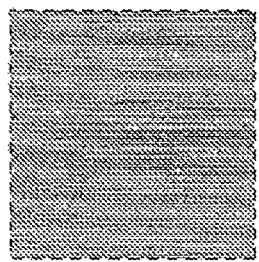

On the use of piezoelectric fibers arranged in parallel, a length change can be achieved along the fiber direction by applying an electrical AC voltage. Such an arrangement can preferably be used for forming compression waves (longitudinal waves) in surfaces of workpieces or components that propagate in the fiber direction (FIG. 3).

The use of fibers in single layers in a common plane for a direct excitation of certain wave modes is part of the prior art. Single-layer transducers using piezoelectric fibers are commercially available.

A formation of SH shear waves in workpieces or components is only possible very ineffectively using the known techniques. There are additionally deficits in the observation of preferred directions of polarization axes so that certain defects, in particular cracks, are not recognized with sufficient reliability.

It is therefore the object of the invention to provide an improved assembly using piezoelectric transducer elements with which an improved formation of shear waves, in particular SH shear waves, is possible by which the sensitivity in nondestructive testing and in state monitoring can be increased.

This object is achieved in accordance with the invention by an assembly of piezoelectric transducers having the features of claim 1. Advantageous embodiments and further developments of the invention can be realized using features designated in subordinate claims.

In the assembly in accordance with the invention for nondestructive material testing with which shear waves can be emitted and detected in elastic surfaces of components or workpieces, piezoelectric transducer elements are arranged above one another in multiple planes and the piezoelectric transducer elements arranged in adjacent planes are each operated oppositely to one another. This means that a lengthening is caused in one plane and a shortening of the length of one or more piezoelectric transducer elements in at least one axial direction is simultaneously caused in the adjacent plane. In this respect, the piezoelectric transducer elements are piezoelectric fibers and/or piezoelectric plate-like elements that are connected to or embedded in an elastically deformable material. The elastically deformable material can be a suitable polymer, e.g. polyimide or polyethylene.

Respective piezoelectric fibers should be aligned in parallel with one another in one plane and piezoelectric fibers should be aligned inclined at an angle to the piezoelectric fibers arranged in the respective other plane in an adjacent plane. An alignment of piezoelectric fibers offset by 90° is preferred in the adjacent planes.

Electrodes having an alignment inclined at an angle to the longitudinal fiber axes of both planes can be present at piezoelectric fibers arranged in adjacent planes.

The electrodes should preferably be oriented inclined by 45° with respect to the fiber axes.

Electrodes having an alignment respectively inclined at an angle to one another can be present at plate-like piezoelectric elements arranged in adjacent planes. The electrodes can be aligned in a similar manner to the piezoelectric fibers.

There is the option with the invention to use correspondingly aligned piezoelectric fibers in one plane and a plate-like piezoelectric transducer element in an adjacent plane.

A plurality of electrodes arranged at a spacing from one another can be present at the individual piezoelectric transducer elements, that is fibers and platelets. The electrodes preferably have spacings of different amounts from one another.

The assembly can preferably be rectangular or square.

Plate-like piezoelectric transducer elements should have a thickness with which a stretching or shortening can be achieved in at least one axial direction with an applied electric voltage and/or formation of at least one electrical field. The thickness of a plate-like piezoelectric transducer element can thus be changed by the acting forces such that the thickness is reduced and a lengthening of the plate-like transducer element is achieved on a compression. With a correspondingly opposite force effect of one or more electrical fields, the thickness can be increased, which results in a shortening.

An assembly in accordance with the invention can be permanently connected to a workpiece or component with material continuity and/or with shape matching such that a permanent testing and monitoring of the state is possible.

The invention utilizes the relationships known from laminate theory additionally to achieve anisotropy in the transducer assembly by the arrangements of piezoelectric fibers in different orientations and/or plate-like elements and in a plurality of layers and thus directly to allow deformations of the assembly and of the transducer elements that are not possible (homogeneously) in the solid material.

Shear can likewise be achieved by the use of fibers placed in specific directions with respect to one another or by the direct electrode structuring.

A shear along a diagonal can be achieved by the use of two layers of piezoelectrically active materials that are, for example, oriented along the diagonal with a square base surface of the transducer by applying oppositely oriented electrical fields of the two layers. A shear along the other diagonal can be achieved by reversing the sign/polarity of the respective electrical fields.

The function described here for the direct piezoelectric effect (deformation by applying an electric voltage) is reversible (inverse effect, electric voltage as a result of shear deformation).

Like other piezoelectric transducers, an assembly in accordance with the invention can be used statically and/or dynamically to excite or to detect elastic waves.

The invention will be explained in more detail by way of example in the following.

Figure 2:
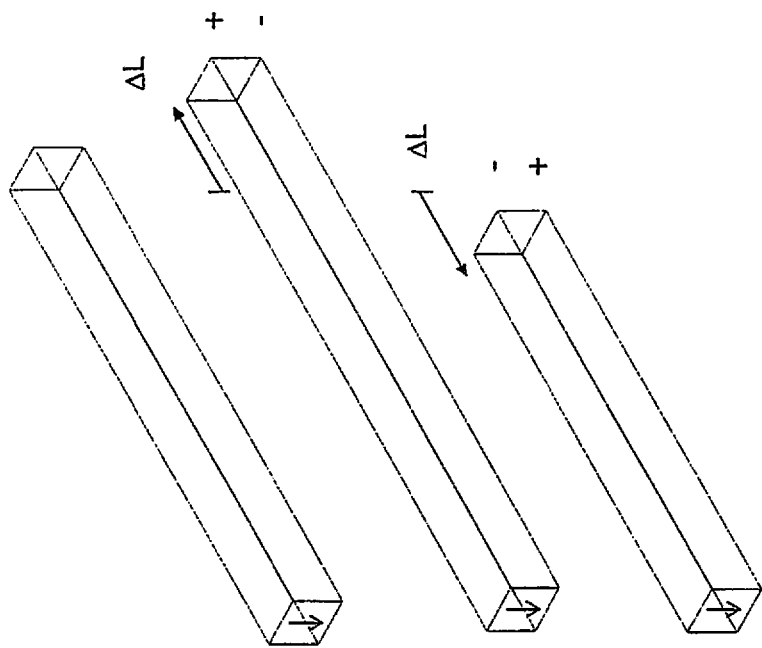
Figure 2:
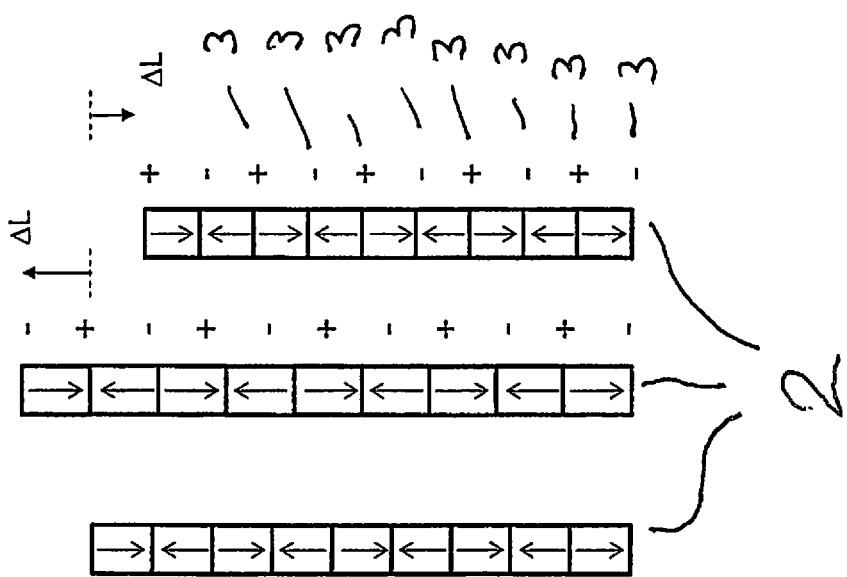
Figure 4:
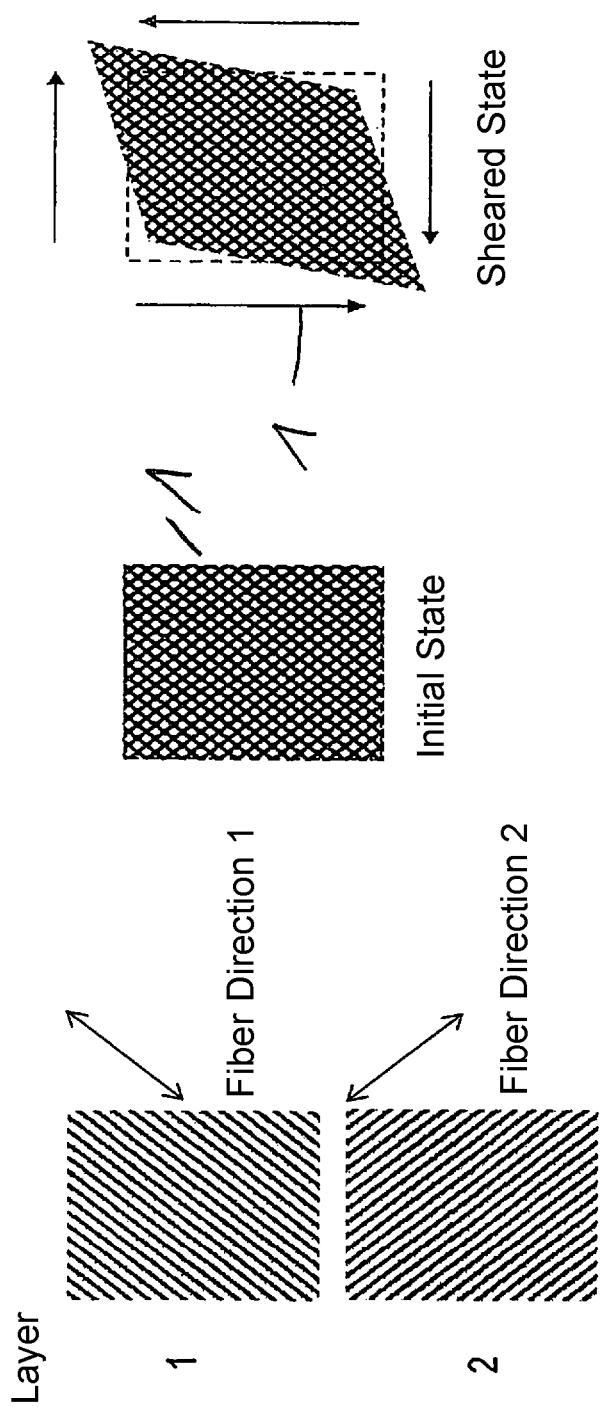

There are shown:

FIG. 1 in a schematic perspective representation, possible deformations that can be caused by the influence of electrical fields at a cube-like piezoelectric transducer element;

FIG. 2 possibilities for an electrical control across a plurality of electrodes at a piezoelectric transducer element that can be used in the invention;

FIG. 3 possibilities for forming compression waves using a plurality of piezoelectric fibers arranged in one plane and in parallel with one another; and FIG. 4 an example of an assembly in accordance with the invention in which piezoelectric fibers are present in parallel with one another in one plane and piezoelectric fibers having different angular alignments are present in an adjacent plane.

An example of a piezoelectric transducer element 2 is shown in FIG. 2 that can be a fiber or of plate form and in which a plurality of electrodes 3 at which a respective electric voltage can be applied are arranged over the length. No electric voltage is applied in the left representation so that the transducer element 2 has the length L. In the two states show further to the right, electric voltages are applied to the electrodes 3 so that the length L is lengthened by an amount ΔL in the middle representation and is shortened by ΔL in the right representation.

Possible deformations of piezoelectric fibers are shown in FIG. 3 that are arranged in parallel with one another and in one plane. In the starting state, a square shape is observed; with electric voltages correspondingly applied at electrodes, the piezoelectric fibers can be lengthened (middle representation) so that a rectangular shape is achieved. On a different connection of electric voltage, the piezoelectric fibers shorten (right representation), whereby in turn a rectangular shape is achieved that, however, has different edge lengths in contrast with the middle representation.

A possibility is shown in FIG. 4 for an assembly in accordance with the invention that is formed with piezoelectric fibers, schematically, with a starting state and with a state that can be achieved by deformation and in which SH shear waves can be emitted.

At the far left in FIG. 4, a plurality of piezoelectric fibers are shown arranged in parallel with one another and with their fiber alignment in two planes schematically above one another as layer 1 and layer 2. It can clearly be recognized that the alignment of the fibers in the two planes, that is layer 1 and layer 2, is selected as perpendicular to one another. Both layers are arranged above one another for an assembly 1 in accordance with the invention, which can be seen schematically from the middle representation, and represents the starting state in which no electrical field is active and no electric voltages are connected. If, however, an electric voltage is applied and at least one electrical field is active, the piezoelectric fibers shorten in one plane (layer 1), while they are simultaneously lengthened in the other plane (layer 2). A deformation is thereby effected such as is shown in the right-hand representation of FIG. 4. With a corresponding coupling or fastening of such an assembly 1, SH shear waves can be emitted into a workpiece or component when the deformation changes multiple times between the deformed state and the starting state, which can be achieved by corresponding influencing of the electric voltage. The direction of the deformation can be influenced in the different planes by the selection of the shortening or lengthening of the piezoelectric transducer elements 2 that are the fibers in this case. A lengthening in the upper plane at one time can thus be selected with a shortening in the lower plane or correspondingly vice versa in the planes.

An assembly 1 in accordance with the invention can in this respect be pressed with sufficient force against a surface of a workpiece or component. There is, however, also the option, as addressed in the general part of the description, of fastening the assembly 1 thereto with material continuity and/or with shape matching.

In principle, a respective corresponding plate-like piezoelectric transducer element can also be used in the planes, with it being shortened in the one plane by connection of an electric voltage and simultaneously a plate-like piezoelectric element being lengthened in the plane arranged above or below it.

The invention claimed is:

1. An assembly for nondestructive material testing with which shear waves are emitted and detected in elastic surfaces of components or workpieces, said assembly including piezoelectric transducer elements arranged above one another in multiple planes, wherein the piezoelectric transducer elements arranged in adjacent planes can each be operated oppositely to one another, wherein said piezoelectric transducer elements are formed from at least one of piezoelectric fibers and piezoelectric plate-like elements that are connected to or embedded in an elastically deformable material.

2. An assembly in accordance with claim 1, wherein said piezoelectric fibers that may be included within at least one of said adjacent planes of said piezoelectric transducer elements are respectively aligned in parallel with one another and piezoelectric fibers in an adjacent plane are aligned inclined at an angle to the piezoelectric fibers that are arranged in the respective other plane.

3. An assembly in accordance with claim 2, characterized in that electrodes having an alignment inclined at an angle to the longitudinal fiber axes of both planes are present at piezoelectric fibers arranged in adjacent planes.

4. An assembly in accordance with claim 1, characterized in that electrodes having an alignment inclined at a respective angle to one another are present at plate-like piezoelectric elements arranged in adjacent planes that may be included within said piezoelectric transducer elements.

5. An assembly in accordance with claim 1, further comprising a plurality of electrodes arranged at a spacing from one another at each of the individual piezoelectric transducer elements.

6. An assembly in accordance with claim 5, characterized in that the spacings between electrodes are of different sizes.

7. An assembly in accordance with claim 1, characterized in that the assembly is rectangular or square.

8. An assembly in accordance with claim 1, characterized in that said plate-like elements that may be included within said piezoelectric transducer elements have a thickness with which a stretching or shortening can be achieved in at least one axial direction with an applied electric voltage and/or on formation of at least one electrical field.

9. An assembly in accordance with claim 1, characterized in that the assembly is permanently connected to a workpiece or component with material continuity and/or with shape matching.

* * * * *